United States Patent

Faulks et al.

[11] Patent Number: 5,356,403
[45] Date of Patent: Oct. 18, 1994

[54] ABSORBENT STRUCTURE COMPRISING A FIBROUS MATRIX HAVING DUAL Z-DIRECTIONAL GRADIENT

[75] Inventors: Michael J. Faulks, Neenah; Daniel R. Schlinz, Appleton, both of Wis.

[73] Assignee: Kimberly-Clark Corporation, Neenah, Wis.

[21] Appl. No.: 982,806

[22] Filed: Nov. 30, 1992

[51] Int. Cl.$^5$ .................. A61F 13/15; A61F 13/20
[52] U.S. Cl. .................. 604/378; 604/358; 604/368; 604/385.1; 604/382
[58] Field of Search .............. 604/358, 368, 378, 379, 604/380, 381, 382, 384, 385.1

[56] References Cited

U.S. PATENT DOCUMENTS

| | | |
|---|---|---|
| 4,102,340 | 7/1978 | Mesek et al. |
| 4,461,621 | 7/1984 | Karami et al. |
| 4,596,567 | 6/1986 | Iskra .................. 604/368 |
| 4,673,402 | 6/1987 | Weisman et al. |
| 4,685,915 | 8/1987 | Hasse et al. |
| 4,699,619 | 10/1987 | Bernardin . |
| 4,699,823 | 10/1987 | Kellenberger et al. .......... 604/368 |
| 4,701,172 | 10/1987 | Stevens . |
| 4,994,037 | 2/1991 | Bernardin . |
| 5,009,650 | 4/1991 | Bernardin . |
| 5,176,668 | 1/1993 | Bernardin . |
| 5,188,624 | 2/1993 | Young, Sr. et al. .......... 604/368 |

FOREIGN PATENT DOCUMENTS

2175024  11/1986  United Kingdom .

*Primary Examiner*—Randall L. Green
*Assistant Examiner*—P. Zuttarelli
*Attorney, Agent, or Firm*—Thomas J. Mielke

[57] ABSTRACT

Disclosed is an absorbent structure containing a fibrous matrix having a dual Z-directional gradient wherein the concentration of high-absorbency material decreases from a first planar surface of the fibrous matrix to the opposed second planar surface, while the density of the fibrous matrix increases from said first major planar surface to the second planar surface. Also disclosed is an absorbent article containing such an absorbent structure.

53 Claims, 3 Drawing Sheets

ABSORBENT STRUCTURE COMPRISING A FIBROUS MATRIX HAVING DUAL Z-DIRECTIONAL GRADIENT

BACKGROUND OF THE INVENTION

1. Field of the Invention

The present invention relates to absorbent structures suitable for use in absorbent products. Specifically, the present invention relates to an absorbent structure having a dual Z-direction gradient.

2. Description of the Related Art

Absorbent structures suitable for use in absorbent products are known. Typically, such absorbent structures comprise an absorbent fibrous matrix such as a batt of comminuted wood pulp fluff. In order to enhance the absorbent capacity of such absorbent structures, it is common to incorporate into them a high-absorbency material known as a superabsorbent material. Such high-absorbency materials are generally capable of absorbing at least about 10, preferably about 15, and most preferably at least about 20 and up to 100 times their weight in water.

In order to enhance the fluid handling capability of absorbent structures formed from a wood pulp fluff matrix, it is known to provide the wood pulp fluff matrix with a Z-direction density gradient. Reference to a Z-direction refers to the thickness of a given fibrous matrix. That is, a fibrous matrix generally comprises first and second opposed major planar surfaces. The first and second opposed major planar surfaces define the length and width (X and Y direction) of the fibrous matrix. The Z-direction refers to the distance separating the first and second major planar surfaces (thickness).

For example, U.S. Pat. No. 5,009,650 issued Apr. 23, 1991, to Bernardin describes an absorbent structure having a fibrous upper layer and a fibrous lower layer. The upper layer has a density of from about 0.03 to about 0.14 gram per cubic centimeter, and the lower layer has a density of from about 0.14 to about 0.3 gram per cubic centimeter. Thus, it is seen that Bernardin describes a fibrous matrix comprising an upper and a lower layer wherein there is a density gradient in the fibrous matrix defined by the low density upper layer and the high density lower layer. Such a structure is said to be well suited for quickly absorbing a liquid discharged on the upper layer and transferring the liquid to a lower layer where the liquid is transported away from the point of discharge.

Similarly, U.S. Pat. No. 4,699,823 issued Oct. 13, 1987, to Kellenberger et al. describes a nonlayered absorbent structure having a Z-directional superabsorbent concentration gradient. Kellenberger describes a fibrous matrix of wood pulp fluff containing superabsorbent particles disposed therein. The concentration of superabsorbent particles dispersed within the fibrous matrix is said to increase from one planar surface of the fibrous matrix to the opposite planar surface. This arrangement of superabsorbent material is said to prevent gel blocking when the planar surface, having a relatively low concentration of superabsorbent particles, is positioned nearest the body of a wearer.

While both density gradients and superabsorbent gradients are known in the art and have proven effective in improving the performance of absorbent products, it is desired to further optimize absorbent structures suited for use in absorbent products.

SUMMARY OF THE INVENTION

In one aspect, the present invention relates to an absorbent structure. The absorbent structure comprises a fibrous matrix having a first major planar surface, a second major planar surface, and a thickness separating said first and second major planar surfaces. The fibrous matrix contains a high-absorbency material. A first one-half of the thickness of the fibrous matrix containing the first major planar surface comprises a greater concentration of high-absorbency material and has a lower average density than a second one-half of the thickness of the fibrous matrix containing the second major planar surface.

In a second aspect, the present invention relates to an absorbent article. The absorbent article comprises an outer cover, a liquid-permeable bodyside liner, and an absorbent structure located between the outer cover and the bodyside liner. The absorbent structure comprises a fibrous matrix having a first major planar surface, a second major planar surface, and a thickness separating said first and second major planar surfaces. The fibrous matrix contains a high-absorbency material. The fibrous matrix is characterized in that a first one-half of the thickness of the fibrous matrix containing said first major planar surface comprises a greater concentration of high-absorbency material and has a lower average density than a second one-half of the thickness of said fibrous matrix containing said second major planar surface. In a preferred embodiment, the first major planar surface is closer to said bodyside liner than the second major planar surface.

DETAILED DESCRIPTION OF THE PREFERRED EMBODIMENT

The present invention relates to an absorbent structure suitable for use in absorbent articles such as diapers, training pants, feminine care products, adult incontinence products, wound dressings, and the like. While the preferred embodiment of the invention will be described in terms of the use of the absorbent structure in an infant diaper, it is to be understood that the absorbent structure is equally suited for use in other absorbent articles known to those skilled in the art.

The absorbent structures of the present invention comprise a fibrous matrix including a high-absorbency material. The fibrous matrix has a dual Z-directional gradient. Specifically, the fibrous matrix has a Z-directional density gradient and a Z-directional high-absorbency material concentration gradient. As used herein, reference to the Z-direction refers to the thickness of the fibrous matrix of the absorbent structure. That is, the fibrous matrix of the present invention has a first major planar surface, a second opposed major planar surface, and a thickness separating the first and second major planar surfaces. The first and second major planar surfaces define the length and width (X and Y dimensions) of the fibrous matrix. The distance separating the first and second major planar surfaces defines the thickness, or Z-direction, of the fibrous matrix. As will be understood by those skilled in the art, the Z-direction is generally perpendicular to the first and second major planar surfaces of the fibrous matrix.

The fibrous matrix is characterized in that a first one-half of the thickness of the fibrous matrix containing the first major planar surface comprises a greater concentration of high-absorbency material and has a lower average density than a second one-half of the thickness of the fibrous matrix containing said second major planar surface.

As used herein, reference to the average density refers to the average of a representative sample of density measurements taken across the length and width of the fibrous matrix. The density is determined under a load of 0.2 pound per square inch.

The fibrous matrix of the present invention can be formed from a wide variety of materials. For example, the fibrous matrix is suitably formed from natural or synthetic fibers. Suitable natural fibers include wood pulp fluff, cotton linters, cotton, bagasse fibers, and the like. Suitable synthetic fibers include melt blown and spunbond polymeric fibers such as those formed from polyolefins, polyamides, polyurethanes and the like. Manmade fibers, such as rayon and cellulose acetate fibers, are also suitable for use in forming the fibrous matrix. Combinations of natural, synthetic and/or manmade fibers are also suitable for use. In one preferred embodiment of the present invention, the fibrous matrix comprises wood pulp fluff.

The fibrous matrix may be formed by air laying fibers, through a spunbond or meltblown process, through a carding process, through a wet laid process, or through essentially any other means, known to those skilled in the art, for forming a fibrous matrix.

The fibrous matrix contains a high-absorbency material commonly known in the art as a superabsorbent. Such high-absorbency materials are generally capable of absorbing at least about 10, preferably about 20, and up to 100 times their weight in water. The high-absorbency material may be formed from an organic material, which may include natural materials such as agar, pectin, and guar gum, as well as synthetic materials such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyrridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Crosslinking may, for example, be by irradiation or covalent, ionic, van der Waals, or hydrogen bonding. Suitable materials are available from various commercial vendors such as the Dow Chemical Company, Hoechst-Celanese Corporation, Allied Colloid, Inc. and Stockhausen, Inc. In one preferred embodiment of the present invention, the high-absorbency material is an alkali metal salt of polyacrylic acid or a starch grafted alkali metal salt of polyacrylic acid.

The high-absorbency material is contained within the fibrous matrix. Methods of incorporating the high-absorbency material into the fibrous matrix are known to those skilled in the art. Suitable methods include incorporating the high-absorbency material into the matrix during formulation of the matrix, such as by air laying the fibers of the fibrous matrix and the high-absorbency material at the same time or wet laying the fibers of the fibrous matrix and the high-absorbency material at the same time. Alternatively, it is possible to apply the high-absorbency material to the fibrous matrix after formation of the fibrous matrix. Other methods include sandwiching the high-absorbency material between two sheets of material, at least one of which is fibrous and liquid permeable. The high-absorbency material may be generally uniformly located between the two sheets of material or may be located in discrete pockets formed by the two sheets.

As described above, the fibrous matrix possesses a Z-directional density gradient and a Z-directional high-absorbency material concentration gradient. As used herein, density refers to the density of the fibrous matrix containing the high-absorbency material; that is, the density of the composite of the fibrous matrix and high-absorbency material. Reference to the high-absorbency concentration refers to the weight percent of high-absorbency materials present in the fibrous matrix based on the weight of the fibrous matrix and high-absorbency material. The portion of the fibrous matrix having a relatively low density is that portion of the fibrous matrix having a relatively high concentration of high-absorbency material. Conversely, the portion of the fibrous matrix having a relatively high density is that portion of the fiber matrix having a relatively low concentration of high-absorbency material. Stated another way, the fibrous matrix has a first major planar surface and a second major planar surface. The thickness of the fibrous matrix separates the first and second major planar surfaces. The one-half of the thickness of the fibrous matrix containing the first major planar surface comprises a greater concentration of high-absorbency material and has a lower average density than the other one-half of the thickness of the fibrous matrix containing the second major planar surface.

The fibrous matrix may be in the form of a single, integrally formed layer or of a composite comprising multiple layers. If the fibrous matrix comprises multiple layers, the layers are in liquid communication with one another such that a liquid present in one fibrous layer can flow or be transported to the other fibrous layer. For example, the fibrous layers may be separated by cellulosic tissue wrap sheets known to those skilled in the art. For the purposes of determining the thickness of a multiple layer fibrous matrix, only those fibrous layers containing fibers and a high-absorbency material should be included. Thus, if the fibrous layers are separated by a fibrous layer not containing a high-absorbency material, the thickness of that layer is not included in determining the thickness of the fibrous matrix.

When the fibrous matrix comprises two or more separately formed fibrous layers containing a high-absorbency material, one of the layers will have a lower average density than the other layer and will have a higher concentration of high-absorbency material than the other layer. The high-absorbency material may be distributed in the individual layers in a generally uniform manner or may be present in the fibrous layers as a layer or other nonuniform distribution.

When the fibrous matrix comprises a single integrally formed layer, the concentration of high-absorbency material may increase along the thickness of the fibrous matrix in a gradual nonstepwise fashion or in a more stepwise fashion. Similarly, the density may decrease through the thickness in a nonstepwise manner or in a stepwise manner.

When the fibrous matrix comprises two or more fibrous layers, the fibrous layers may have the same or different basis weights. In one preferred embodiment, the first fibrous layer having a relatively low density and a relatively high concentration of high-absorbency material will have a basis weight of from about 150 to about 1500 grams per square meter, and the second fibrous layer having a relatively high density and low concentration of high-absorbency material will have a basis weight of from about 100 to about 1250 grams per square meter. The first fibrous layer may have a greater basis weight than the second fibrous layer. Specifically, the basis weight of the first fibrous layer may be about 10, beneficially about 20, and preferably about 25 percent greater than the basis weight of the second fibrous layer.

When the fibrous matrix comprises a single integrally formed layer having a gradual, nonstepwise high-absorbency material concentration gradient, localized high-absorbency material concentrations can, for the purposes of this invention, be determined by taking a slice through the fibrous matrix along a plane which is generally perpendicular to the Z-direction to expose a selected layer within the fibrous matrix. The percentage of the exposed area of the matrix covered by particles of high-absorbency material is considered to be the percent areal concentration. Once the percent areal concentration is determined, the weight percent concentration can be calculated by assuming a spherical particle shape, raising the percent areal concentration to the 3/2 power and by taking into account the densities of the different materials within the slice.

Further, once the thickness of the fibrous matrix, either single layer or multiple layers, is determined, the fibrous matrix can be divided in one-half of its thickness by slicing the fibrous matrix at the calculated location along a plane perpendicular to the Z-direction of the fibrous matrix. The average densities of the various halves of the fibrous matrix are then determined by taking a representative number of density determinations across the length and width of the fibrous matrix. An average density is then calculated. The concentration of high-absorbency material present in one-half of the thickness of the fibrous matrix can be analytically determined. For example, when the high-absorbency material comprises a sodium salt of polyacrylic acid, the concentration of high-absorbency material in the various halves can be determined through sodium ash testing.

The first one-half of the thickness of a fibrous matrix containing the first major planar surface suitably comprises from about 20 to about 95, beneficially from about 20 to about 50 weight percent of the high-absorbency material based on total weight of the fiber matrix and high-absorbency material present in said first one-half of the thickness of the fibrous matrix. The first one-half of the fibrous matrix containing the first major planar surface suitably has a density of from about 0.01 to about 0.2, beneficially from about 0.05 to about 0.2 gram per cubic centimeter.

The second one-half of the thickness of the fibrous matrix containing the second major planar surface suitably comprises from about 5 to about 50, beneficially of from about 5 to about 35 weight percent of the high-absorbency material based on total weight of the fibrous matrix and high-absorbency material present in said second one-half of the thickness of the fibrous matrix. The second one-half of the fibrous matrix containing the second major planar surface suitably has a density of from about 0.1 to about 0.4, beneficially of from about 0.15 to about 0.35 gram per cubic centimeter.

The absorbent structures of the present invention are suitably used in absorbent articles. Such absorbent articles generally comprise a liquid-permeable bodyside liner, an outer cover, and an absorbent structure, such as the absorbent structures of the present invention, located between the bodyside liner and outer cover. It is generally preferred that the first one-half of the fibrous matrix containing the first major planar surface and having a relatively low density and a relatively high concentration of high-absorbency material be located closer to the liquid-permeable bodyside liner than the other one-half of the thickness of the fibrous matrix. That is, it is preferred that the highest concentration of high-absorbency material and lowest density portion of the fibrous matrix be located closest to the bodyside liner and to the body of a wearer in use. Applicants have found that the high-absorbency materials of the present invention are generally capable of dewatering the fibrous matrix to such an extent that the surface of the fibrous matrix containing a relatively high concentration of high-absorbency material has a relatively drier feel than the surface of the fibrous matrix containing a relatively low concentration of high-absorbency material. Accordingly, it is preferred to place the drier surface of the fibrous matrix closest to the body of a wearer in use.

When the high-absorbency materials of the present invention are to be employed in the fibrous matrix at concentrations of greater than about 30 percent, it is generally preferred that the high-absorbency materials possess the physical properties described as being desirable in commonly assigned copending U.S. patent application Ser. No. 07/906,001 filed Jun. 26, 1992, in the name of Byerley et al., the specification of which is incorporated herein by reference. Specifically, it is preferred that the high-absorbency material have a Deformation Under Load of less than 0.6 millimeter and a Wicking Index of 10 centimeters. Alternatively, the high-absorbency material may have a Wicking Parameter of 700 or greater or a 0.6 pound per square inch Absorbency Under Load of at least 13 grams per gram.

Figure 1:
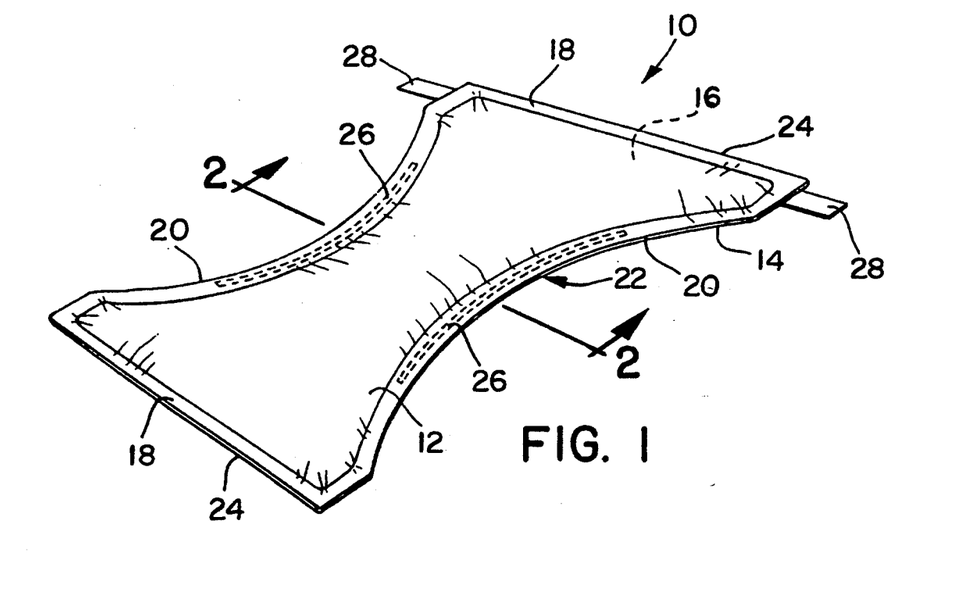
FIG. 1 is a perspective view of an absorbent article according to the present invention.

With reference now to the drawings, wherein like numerals represent like elements, FIG. 1 illustrates a perspective view of disposable diaper 10 including a liquid-permeable bodyside liner 12, an outer cover 14, and an absorbent structure 16 located between the bodyside liner and outer cover. The bodyside liner and outer cover are larger than the absorbent structure and have end marginal portions 18 extending beyond the ends of absorbent structure 16. The bodyside liner and outer cover also have side marginal portions 20 extending beyond the sides of the absorbent structure. Typically, bodyside liner 12 and outer cover 14 are secured to each other along the marginal portions 18 and 20.

The diaper 10 has a generally hourglass or I-shape, which includes a narrow crotch section 22 near the center of the diaper, and includes waistband sections 24 at each end of the diaper. Elongate elastic means 26 are secured in place adjacent absorbent structure 16, and on each side thereof, to develop gathered elastic leg portions that are conformable with an infant's legs. Conventional pressure-sensitive tapes 28 are attached to one waistband section 24. Diaper 10 is fitted to an infant with the bodyside liner 12 against the infant's skin. One waistband portion encircles part of the infant's waist, and the other waistband portion encircles the balance of the infant's waist. The two waistband portions are overlapped and joined together by pressure-sensitive tapes 28 which operate to hold the diaper in place.

Conventional materials are employed for the component elements of diaper 10. Bodyside liner 12 may be any soft, flexible, porous sheet which passes fluids therethrough, and may, for example, be comprised of a nonwoven web or sheet of polyolefin fibers, such as polypropylene fibers. The bodyside liner may also be comprised of wet strength tissue papers, a spunbond filament sheet, or the like. In addition, the liner may be treated with a surfactant to aid in liquid transfer.

Outer cover 14 is suitably formed from a liquid-impermeable layer and may be comprised of a thin web or sheet of plastic film, such as polyethylene, polypropylene, polyvinyl chloride, or the like. The absorbent structure 16 is suitably that described above. Bodyside liner 12, outer cover 14, and absorbent structure 16 may be combined with one another in any suitable manner to form the finished diaper. The elements may be bonded to one another by strips or patterns of hot melt or pressure-sensitive adhesive, overall or patterned heat sealing, strips of double-faced, pressure-sensitive adhesive tapes or the like. A particularly effective bonding system employs spaced, parallel lines of hot melt adhesive placed on the interior surface of outer cover 14. The absorbent structure is bonded to the outer cover along portions of the adhesive lines, and bodyside liner 12 is bonded to outer cover 14 along other portions of the adhesive lines that are located within the marginal portions 18 and 20 but outside the region of absorbent structure 16.

Figure 2:
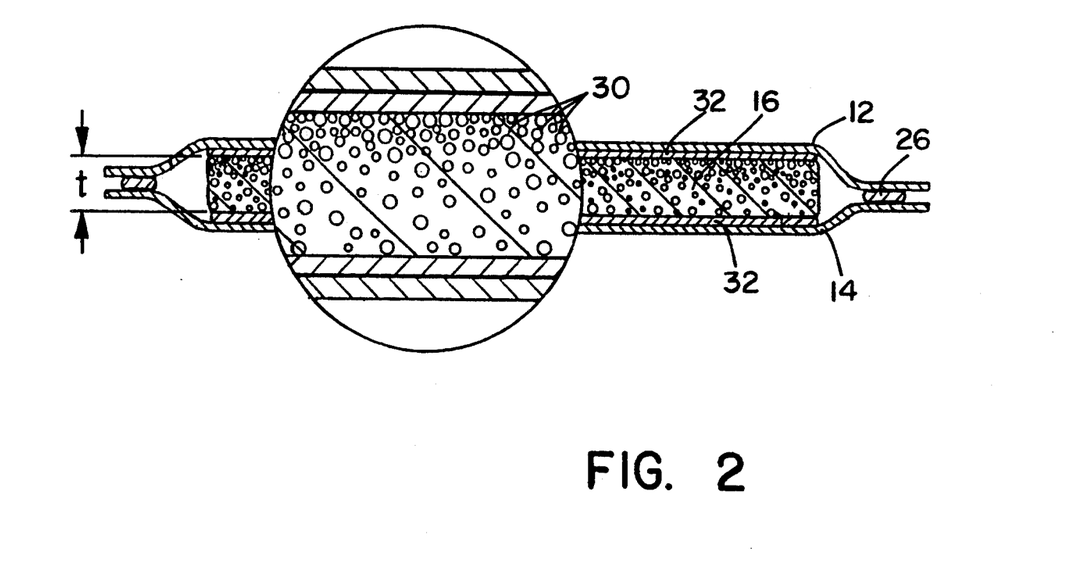
FIG. 2 is a cross-sectional view of the absorbent article illustrated in FIG. 1, taken along line 2—2.

FIG. 2 is a cross-sectional view of the diaper illustrated in FIG. 1 taken along line 2—2. As can be seen from reference to FIG. 2, absorbent structure 16 comprises a single, integrally formed fibrous web containing particulate high-absorbency materials 30. As can be seen from reference to FIG. 2, one-half of the thickness "t" of absorbent structure 16 comprises a greater concentration of high-absorbency material particles 30 than the other half of the thickness of the fibrous matrix. Absorbent structure 16 further comprises tissue wrap sheets 32. The one-half of the thickness of the fibrous matrix closest to the bodyside liner 12 comprises the greater concentration of high-absorbency material particles. It is seen, from reference to FIG. 2, that the concentration of high-absorbency material particles gradually decreases as one moves through the thickness of the fibrous matrix. It is understood that the one-half of the thickness of the fibrous matrix containing the greater concentration of high-absorbency material particles similarly possesses a lower average density compared to the other half of the fibrous matrix.

Figure 3:
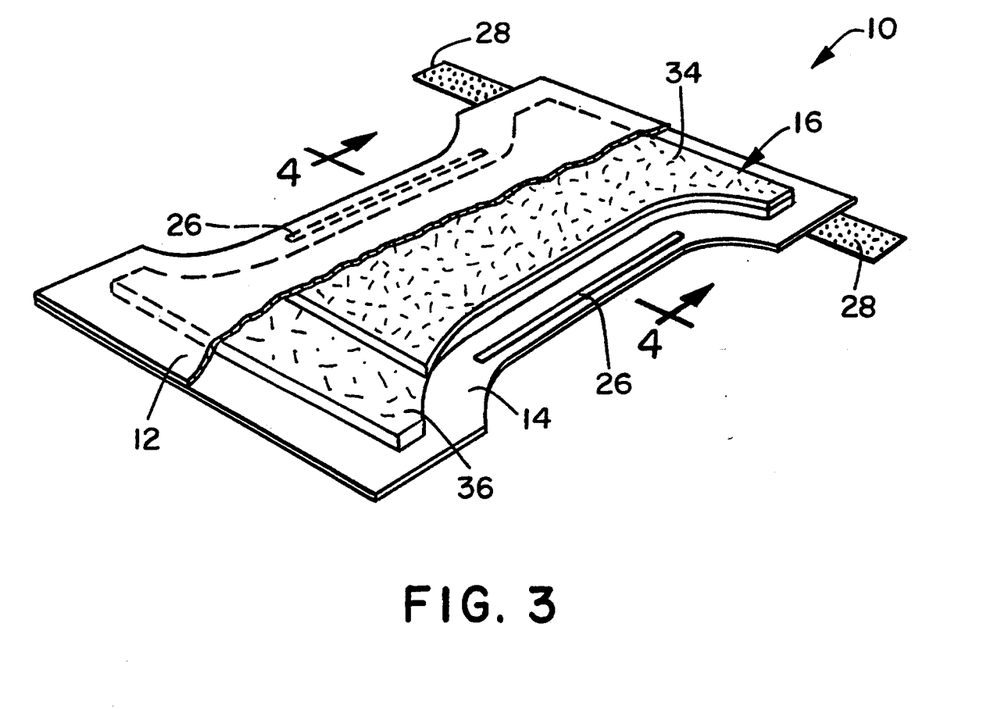
FIG. 3 is a cut-away perspective view of an absorbent article according to the present invention.
Figure 4:
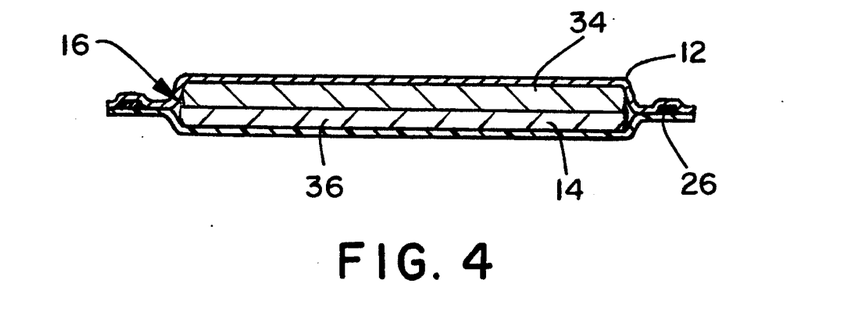
FIG. 4 is a cross-sectional view of the article illustrated in FIG. 3 taken along line 4—4.
Figure 5:
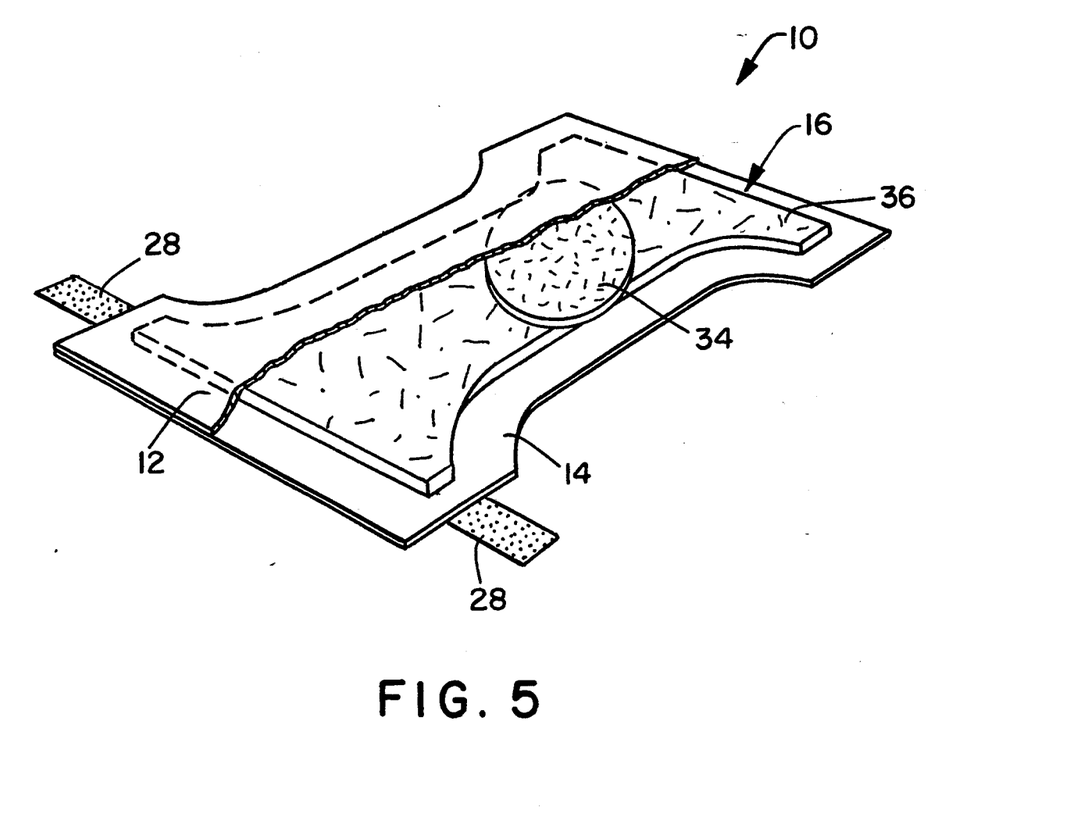
FIG. 5 is a cut-away perspective view of an absorbent article according to the present invention.

FIGS. 3–5 illustrate the situation wherein the fibrous matrix comprises two or more fibrous layers. With reference to FIGS. 3 and 4, disposable diaper 10 comprises a bodyside liner 12, an outer cover 14, and an absorbent structure 16 located between the bodyside liner and outer cover 14. The absorbent structure 16 comprises a first fibrous layer 34 and a second fibrous layer 36. As can be seen from reference to FIGS. 3 and 4, the first fibrous layer 34 extends along the length of the product to a lesser extent than the second fibrous layer 36. The first fibrous layer 34 is substantially the same width as the second fibrous layer 36 but covers only a portion of the length of the second fibrous layer 36. The first fibrous layer 34 is positioned closer to bodyside liner 12 than the second fibrous layer 36. The first fibrous layer 34 comprises a fibrous matrix containing a high-absorbency material. First fibrous layer 34 contains a greater concentration of high-absorbency material particles than the second fibrous layer 36. Further, first fibrous layer 34 has a lower average density and a greater basis weight than second fibrous layer 36. Due to the greater basis weight of the first fibrous layer 34, one-half of the thickness of the fibrous matrix comprising first fibrous layer 34 and second fibrous layer 36 does not occur at the interface of the first and second fibrous layers but, instead, would occur somewhere within the thickness of the first fibrous layer 34.

FIG. 5 illustrates a third embodiment of the present invention wherein the first fibrous layer 34 comprises a pledget placed in the target area of the diaper 10 where liquid waste initially accumulates.

Examples and Comparative Examples

The following absorbent structures are prepared:

Absorbent Structure 1—An airlaid mixture of 65 weight percent wood pulp fluff (20 percent hardwood, 80 percent softwood) and 35 weight percent of a high-absorbency material (commercially available from Hoechst-Celanese Corporation under the trade designation IM-3900) is prepared. The absorbent structure has a basis weight (fluff and high-absorbency material) of 640 grams per square meter and a density of 0.2 gram per cubic centimeter. The absorbent structure is cut in an I-shape having a length of 13.5 inches, a width at the longitudinal ends of 7.0 inches, and a width in the crotch section of about 2.5 inches.

Absorbent Structure 2—This absorbent structure comprises two fibrous layers. The first, upper layer (closest to body of wearer during use), is an airlaid mixture of wood pulp fluff and a high-absorbency material. The upper fibrous layer comprises 35 weight percent of the high-absorbency material and 65 weight percent of the wood pulp fluff employed in forming absorbent structure 1. The upper layer has a basis weight of 505 grams per square meter and a density of 0.2 gram per cubic centimeter. The upper layer has a modified-T shape having a length of 8.25 inches, a width in the front of 7 inches, a width in the back of 3.5 inches and a width in the crotch of 2.5 inches. The upper layer is centered within the width and length of the lower layer. The lower layer comprises an airlaid mixture of the wood pulp fluff (65 weight percent) and high-absorbency material (35 weight percent) employed in absorbent structure 1. The lower layer has a basis weight of 360 grams per square meter and a density of 0.2 gram per cubic centimeter. The lower layer has the same I-shape as absorbent structure 1.

Absorbent Structure 3—This absorbent structure has a two-layer configuration and is formed from the same materials as absorbent structures 1 and 2. The upper layer is airlaid and comprises 35 weight percent of the high-absorbency material and 65 weight percent of the wood pulp fluff. The upper layer has a basis weight of 615 grams per square meter and a density of 0.2 gram per cubic centimeter. The lower layer comprises 35 weight percent of the high-absorbency material and 65 weight percent of the wood pulp fluff. The lower layer has a basis weight of 250 grams per square meter, and a density of 0.2 gram per cubic centimeter. The upper and lower layers have the same shape as the upper and lower layers, respectively, of absorbent structure 2.

Absorbent Structure 4—This absorbent structure has a two-layer configuration and is formed from the same materials as absorbent structures 1-3. The upper layer comprises 35 weight percent of the high-absorbency material and 65 weight percent of the wood pulp fluff. The upper layer has a basis weight of 615 grams per square meter and a density of 0.2 gram per cubic centimeter. The lower layer comprises 25 weight percent of the high-absorbency material and 75 weight percent of the wood pulp fluff. The lower layer has a basis weight of 310 grams per square meter, and a density of 0.3 gram per cubic centimeter. The upper and lower layers have the same shape as the upper and lower layers, respectively, of absorbent structure 2.

Absorbent structures 1 and 2 have an absorbent capacity of approximately 400 cubic centimeters. Absorbent structure 3 has an absorbent capacity of approximately 370 cubit centimeters. Absorbent structure 4 has an absorbent capacity of approximately 385 cubic centimeters. As can be appreciated from reference to the description of the absorbent structures, absorbent structures 1, 2, and 3 are not absorbent structures according to the present invention but are employed for comparison. Absorbent structure 4 is the only described absorbent structure according to the present invention and represents a preferred embodiment thereof.

Each of the absorbent structures is placed in the chassis of a diaper commercially available from the Kimberly-Clark Corporation under the trade designation HUGGIES ® disposable diapers (medium size) for testing. Specifically, the commercially available HUGGIES brand disposable diaper has the bodyside liner and absorbent structure contained within the commercially available diaper removed. The absorbent structures 1-4 described above are then inserted into the diaper chassis in place of the absorbent structure originally present therein. The absorbent structures 1-4 are adhered to the outer cover of the commercially available diaper with double-sided adhesive tape. A bodyside liner having a basis weight of 50 grams per square meter is then placed over the absorbent structures in the same manner as the original bodyside liner. The bodyside liner is a bonded carded web and is formed from 1.5 inch, 1.8 denier per filament bicomponent fibers having an inner core of polypropylene and an outer sheath of polyethylene. The diaper is then subjected to a forced leakage test.

Specifically, each of the diapers is applied to a flexible baby torso sized appropriately for a medium-size diaper. The flexible baby torso is adapted to apply a liquid to the bodyside liner of the diaper at a position generally centered on the width of the diaper and approximately 5.0 inches below the front waistband of the diaper when it is in place on the torso. An aqueous solution containing 0.9 weight percent sodium chloride is applied through a nozzle located in the torso at a rate of about 15 cubic centimeters per second. After an initial application of 60 milliliters, 30 milliliters of the sodium chloride solution are applied at 10 minute intervals. The flexible baby torso is pneumatically manipulated in a manner to simulate leg movement at spaced intervals during the course of the forced leakage test. Moisture sensors located around the periphery of the diaper indicate the time at which leakage occurs. As soon as leakage is detected, the test is stopped and the total amount of sodium chloride solution applied to the diaper up to the time of leakage is recorded. The results of this testing are set forth in Table 1. The results represent the average of three trials for each absorbent structure and the standard deviation for the three trials is indicated.

TABLE 1

| Absorbent Structure | Load at Leakage (ml) | Std. Deviation |
|---|---|---|
| 1* | 201 | 17.4 |
| 2* | 242 | 0.6 |
| 3* | 274 | 1.5 |
| 4 | 293 | 17.7 |

*Not an example of the present invention

As can be seen from reference to Table 1, the absorbent structure according to the present invention produces a diaper having a higher degree of performance as measured by the forced leakage test.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. An absorbent structure, said absorbent structure comprising:
   a fibrous matrix having a first one-half comprising a first major planar surface, and a second one-half comprising a second opposed major planar surface, said first one-half and said second one-half of said fibrous matrix containing a high-absorbency material, said fibrous matrix being characterized in that the first one-half of said fibrous matrix containing said first major planar surface comprises a greater concentration of high-absorbency material and has a lower average density than the second one-half of said fibrous matrix containing said second major planar surface and wherein said first one-half of said fibrous matrix comprises from about 20 to about 95 weight percent of said high-absorbency material based on a total weight of the fibrous matrix and high-absorbency material present in said first one-half of the fibrous matrix.

2. An absorbent structure according to claim 1 wherein said first one-half of said fibrous matrix has a density of from about 0.01 to about 0.2 grams per cubic centimeter.

3. The absorbent structure according to claim 1 wherein said second one-half of said fibrous matrix comprises from about 5 to about 50 weight percent of said high-absorbency material based on a total weight of the fibrous matrix and high-absorbency material present in said second one-half of the fibrous matrix.

4. The absorbent structure according to claim 1 wherein said second one-half of said fibrous matrix has a density of from about 0.1 to about 0.4 grams per cubic centimeter.

5. The absorbent structure according to claim 1 wherein said first one-half of said fibrous matrix comprises from about 20 to about 50 weight percent of said high-absorbency material.

6. The absorbent structure according to claim 2 wherein said first one-half of said fibrous matrix has a density of from about 0.05 to about 0.2 grams per cubic centimeter.

7. The absorbent structure according to claim 3 wherein said second one-half of said fibrous matrix comprises from about 5 to about 35 weight percent of said high-absorbency material.

8. The absorbent structure according to claim 4 wherein said second one-half of said fibrous matrix has a density of from about 0.15 to about 0.35 grams per cubic centimeter.

9. The absorbent structure according to claim 1 wherein said first one-half of said fibrous matrix has a density of from about 0.01 to about 0.2 grams per cubic centimeter, and said second one-half of said fibrous matrix comprises from about 5 to about 50 weight percent of said high-absorbency material based on a total weight of the fibrous matrix and high-absorbency material present in said second one-half of the fibrous matrix and has a density of from about 0.1 to about 0.4 grams per cubic centimeter.

10. The absorbent structure according to claim 1 wherein said first one-half of said fibrous matrix comprises from about 20 to about 50 weight percent of said high-absorbency material and has a density of from about 0.05 to about 0.2 grams per cubic centimeter and said second one-half of said fibrous matrix comprises from about 5 to about 35 weight percent of said high-absorbency material based on a total weight of the fibrous matrix and high-absorbency material present in said second one-half of the fibrous matrix and has a density of from about 0.15 to about 0.35 grams per cubic centimeter.

11. The absorbent structure according to claim 1 wherein said fibrous matrix comprises first and second separately formed fibrous layers containing a high-absorbency material, said first fibrous layer containing said first major planar surface and having a lower average density and a greater concentration of high-absorbency material than said second fibrous layer containing said second major planar surface.

12. The absorbent structure according to claim 11 wherein said first fibrous layer contains from about 20 to about 95 weight percent of said high-absorbency material based on a total weight of the first fibrous layer and high-absorbency material present in said first fibrous layer and said second fibrous layer contains from about 5 to about 50 weight percent of said high-absorbency material based on a total weight of the second fibrous layer and high-absorbency material present in said second fibrous layer.

13. The absorbent structure according to claim 12 wherein said first fibrous layer has a density of from about 0.01 to about 0.2 grams per cubic centimeter, and said second fibrous layer has a density of from about 0.1 to about 0.4 grams per cubic centimeter.

14. The absorbent structure according to claim 12 wherein said high-absorbency material is substantially uniformly dispersed in said first and second fibrous layers.

15. The absorbent structure according to claim 11 wherein said first fibrous layer has a basis weight of from about 150 to about 1500 grams per square meter and said second fibrous layer has a basic weight of from about 100 to about 1250 grams per square meter, wherein the basis weight of said first fibrous layer is greater than the basis weight of said second fibrous layer.

16. The absorbent structure of claim 1 wherein said fibrous matrix is a single, integrally formed layer containing a high-absorbency material.

17. The absorbent structure according to claim 16 wherein the concentration of high-absorbency material decreases from said first major planar surface to said second major planar surface in a nonstepwise manner.

18. An absorbent article, said article comprising:
an outer cover;
a liquid-permeable bodyside liner; and
an absorbent structure located between said outer cover and said bodyside liner, said absorbent structure comprising:
a fibrous matrix having a first one-half comprising a first major planar surface, and a second one-half comprising a second opposed major planar surface, said first one-half and said second one-half of said fibrous matrix containing a high-absorbency material, the fibrous matrix being characterized in that the first one-half of said fibrous matrix containing said first major planar surface comprises a greater concentration of high-absorbency material and has a lower average density than the second one-half of said fibrous matrix containing said second major planar surface and wherein said first one-half of said fibrous matrix comprises from about 20 to about 95 weight percent of said high-absorbency material based on a total weight of the fibrous matrix and high-absorbency material present in said first one-half of the fibrous matrix.

19. The absorbent article according to claim 18 wherein said first major planar surface is closer to said bodyside liner than said second major planar surface.

20. The absorbent article according to claim 20 wherein said second half of said fibrous matrix comprises from about 5 to about 50 weight percent of said high-absorbency material based on a total weight of the fibrous matrix and high-absorbency material present in said second one-half of the fibrous matrix.

21. The absorbent article according to claim 19 wherein said first one-half of said fibrous matrix has a density of from about 0.01 to about 0.2 grams per cubic centimeter, and said second one-half of said fibrous matrix has a density of from about 0.1 to about 0.4 grams per cubic centimeter.

22. The absorbent structure according to claim 19 wherein said first one-half of said fibrous matrix comprises from about 20 to about 50 weight percent of said high-absorbency material and said second one-half of said fibrous matrix comprises from about 5 to about 35 weight percent of said high-absorbency material based on a total weight of the fibrous matrix and high-absorbency material present in said second one-half of the fibrous matrix.

23. The absorbent article according to claim 19 wherein said first one-half of said fibrous matrix has a density of from about 0.05 to about 0.2 grams per cubic centimeter and said second one-half of said fibrous matrix has a density of from about 0.15 to about 0.35 grams per cubic centimeter.

24. The absorbent article according to claim 19 wherein said fibrous matrix comprises first and second separately formed fibrous layers containing a high-absorbency material, said first fibrous layer containing said first major planar surface and having a lower average density and a greater concentration of high-absorbency material than said second fibrous layer containing said second major planar surface.

25. The absorbent article according to claim 24 wherein said first fibrous layer contains from about 20 to about 95 weight percent of said high-absorbency material based on a total weight of the first fibrous layer and high-absorbency material present in said first fibrous layer and said second fibrous layer contains from about 5 to about 50 weight percent of said high-absorbency material based on a total weight of the second fibrous layer and high-absorbency material present in said second fibrous layer.

26. The absorbent article according to claim 24 wherein said first fibrous layer has a density of from about 0.01 to about 0.2 grams per cubic centimeter, and said second fibrous layer has a density of from about 0.1 to about 0.4 grams per cubic centimeter.

27. The absorbent article according to claim 24 wherein said high-absorbency material is substantially uniformly dispersed in said first and second fibrous layers.

28. The absorbent article according to claim 19 wherein said fibrous matrix is a single integrally formed layer containing a high-absorbency material.

29. The absorbent article according to claim 28 wherein the concentration of said high-absorbency material decreases from said first major planar surface to said second major planar surface in a nonstepwise manner.

30. An absorbent structure, said absorbent structure comprising:
a fibrous matrix having a first one-half comprising a first major planar surface, and a second one-half comprising a second opposed major planar surface, said first one-half and said second one-half of said fibrous matrix containing a high-absorbency material, said fibrous matrix being characterized in that the first one-half of said fibrous matrix containing said first major planar surface comprises a greater concentration of high-absorbency material and has a lower average density than the second one-half of said fibrous matrix containing said second major planar surface and wherein said first one-half of said fibrous matrix has a density of from about 0.01 to about 0.2 grams per cubic centimeter.

31. The absorbent structure according to claim 30 wherein said second one-half of said fibrous matrix comprises from about 5 to about 50 weight percent of said high-absorbency material based on a total weight of the fibrous matrix and high-absorbency material present in said second one-half of the fibrous matrix.

32. The absorbent structure according to claim 30 wherein said second one-half of said fibrous matrix has a density of from about 0.1 to about 0.4 grams per cubic centimeter.

33. The absorbent structure according to claim 30 wherein said first one-half of said fibrous matrix comprises from about 20 to about 50 weight percent of said high-absorbency material based on a total weight of the fibrous matrix and high-absorbency material present in said first one-half of the fibrous matrix.

34. The absorbent structure according to claim 30 wherein said first one-half of said fibrous matrix has a density of from about 0.05 to about 0.2 grams per cubic centimeter.

35. The absorbent structure according to claim 31 wherein said second one-half of said fibrous matrix comprises from about 5 to about 35 weight percent of said high-absorbency material.

36. The absorbent structure according to claim 32 wherein said second one-half of said fibrous matrix has a density of from about 0.15 to about 0.35 grams per cubic centimeter.

37. An absorbent structure, said absorbent structure comprising:
a fibrous matrix having a first one-half comprising a first major planar surface, and a second one-half comprising a second opposed major planar surface, said fibrous matrix containing a high-absorbency material, said fibrous matrix being characterized in that the first one-half of said fibrous matrix containing said first major planar surface comprises a greater concentration of high-absorbency material and has a lower average density than the second one-half of said fibrous matrix containing said second major planar surface and wherein said second one-half of said fibrous matrix comprises from about 5 to about 50 weight percent of said high-absorbency material based on a total weight of the fibrous matrix and high-absorbency material present in said second one-half of the fibrous matrix.

38. The absorbent structure according to claim 37 wherein said second one-half of said fibrous matrix has a density of from about 0.1 to about 0.4 grams per cubic centimeter.

39. The absorbent structure according to claim 37 wherein said first one-half of said fibrous matrix comprises from about 20 to about 50 weight percent of said high-absorbency material based on a total weight of the fibrous matrix and high-absorbency material present in said first one-half of the fibrous matrix.

40. The absorbent structure according to claim 37 wherein said first one-half of said fibrous matrix has a density of from about 0.05 to about 0.2 grams per cubic centimeter.

41. The absorbent structure according to claim 37 wherein said second one-half of said fibrous matrix comprises from about 5 to about 35 weight percent of said high-absorbency material.

42. The absorbent structure according to claim 38 wherein said second one-half of said fibrous matrix has a density of from about 0.15 to about 0.35 grams per cubic centimeter.

43. An absorbent article, said article comprising:
an outer cover;
a liquid-permeable bodyside liner; and
an absorbent structure located between said outer cover and said bodyside liner, said absorbent structure comprising:
a fibrous matrix having a first one-half comprising a first major planar surface, and a second one-half comprising a second opposed major planar surface, said first one-half and said second one-half of said fibrous matrix containing a high-absorbency material, the fibrous matrix being characterized in that the first one-half of said fibrous matrix containing said first major planar surface comprises a greater concentration of high-absorbency material and has a lower average density than the second one-half of said fibrous matrix containing said second major planar surface and wherein said first one-half of said fibrous matrix has a density of from about 0.01 to about 0.2 grams per cubic centimeter.

44. The absorbent article according to claim 43 wherein said first major planar surface is closer to said bodyside liner than said second major planar surface.

45. The absorbent article according to claim 43 wherein said first one-half of said fibrous matrix comprises from about 20 to about 95 weight percent of said high-absorbency material based on a total weight of the fibrous matrix and high-absorbency material present in said first one-half of the fibrous matrix, and said second one-half of said fibrous matrix comprises from about 5 to about 50 weight percent of said high-absorbency material based on a total weight of the fibrous matrix and high-absorbency material present in said second one-half of the fibrous matrix.

46. The absorbent article according to claim 43 wherein said second one-half of said fibrous matrix has a density of from about 0.1 to about 0.4 grams per cubic centimeter.

47. The absorbent structure according to claim 43 wherein said first one-half of said fibrous matrix comprises from about 20 to about 50 weight percent of said high-absorbency material based on a total weight of the fibrous matrix and high-absorbency material present in said first one-half of the fibrous matrix, and said second one-half of said fibrous matrix comprises from about 5 to about 35 weight percent of said high-absorbency material based on a total weight of the fibrous matrix and high-absorbency material present in said second one-half of the fibrous matrix.

48. The absorbent article according to claim 43 wherein said first one-half of said fibrous matrix has a density of from about 0.05 to about 0.2 grams per cubic centimeter and said second one-half of said fibrous matrix has a density of from about 0.15 to about 0.35 grams per cubic centimeter.

49. An absorbent article, said article comprising:
an outer cover;
a liquid-permeable bodyside liner; and
an absorbent structure located between said outer cover and said bodyside liner, said absorbent structure comprising:
a fibrous matrix having a first one-half comprising a first major planar surface, and a second one-half comprising a second opposed major planar surface, said fibrous matrix containing a high-absorbency material, the fibrous matrix being characterized in that the first one-half of said fibrous matrix containing said first major planar surface comprises a greater concentration of high-absorbency material and has a lower average density than the second one-half of said fibrous matrix containing said second major planar surface and wherein said second one-half of said fibrous matrix comprises from about 5 to about 50 weight percent of said high-absorbency material based on a total weight of the fibrous matrix and high-absorbency material present in said second one-half of the fibrous matrix.

50. The absorbent article according to claim 49 wherein said first major planar surface is closer to said bodyside liner than said second major planar surface.

51. The absorbent article according to claim 49 wherein said second one-half of said fibrous matrix has a density of from about 0.1 to about 0.4 grams per cubic centimeter.

52. The absorbent structure according to claim 49 wherein said first one-half of said fibrous matrix comprises from about 20 to about 50 weight percent of said high-absorbency material based on a total weight of the fibrous matrix and high-absorbency material present in said first one-half of the fibrous matrix, and said second one-half of said fibrous matrix comprises from about 5 to about 35 weight percent of said high-absorbency material.

53. The absorbent article according to claim 49 wherein said first one-half of said fibrous matrix has a density of from about 0.05 to about 0.2 grams per cubic centimeter and said second one-half of said fibrous matrix has a density of from about 0.15 to about 0.35 grams per cubic centimeter.

* * * * *